(12) United States Patent
Huang

(10) Patent No.: US 9,205,168 B2
(45) Date of Patent: Dec. 8, 2015

(54) AIR PURIFIER

(76) Inventor: Fu-Kuo Huang, New Taipei (TW)

( * ) Notice: Subject to any disclaimer, the term of this patent is extended or adjusted under 35 U.S.C. 154(b) by 166 days.

(21) Appl. No.: 14/125,147

(22) PCT Filed: Jun. 20, 2011

(86) PCT No.: PCT/CN2011/001021
§ 371 (c)(1),
(2), (4) Date: Mar. 19, 2014

(87) PCT Pub. No.: WO2012/174675
PCT Pub. Date: Dec. 27, 2012

(65) Prior Publication Data
US 2014/0186223 A1    Jul. 3, 2014

(51) Int. Cl.
*A61L 9/00*        (2006.01)
*B01D 53/02*    (2006.01)
*A61L 9/20*        (2006.01)
*B01D 46/00*    (2006.01)

(52) U.S. Cl.
CPC .............. *A61L 9/205* (2013.01); *B01D 46/0039* (2013.01); *A61L 2209/12* (2013.01); *A61L 2209/14* (2013.01)

(58) Field of Classification Search
CPC ............ A61L 9/00; A61L 9/032; A61L 9/037; A61L 9/20
USPC .............................. 422/305–306; 96/108, 224
See application file for complete search history.

(56) References Cited

U.S. PATENT DOCUMENTS

2008/0193326 A1*    8/2008  Mole ................................. 422/2

\* cited by examiner

*Primary Examiner* — Monzer R Chorbaji
(74) *Attorney, Agent, or Firm* — Rosenberg, Klein & Lee

(57) ABSTRACT

The present invention relates to an air purifier, comprising a housing, an air dynamic unit, an ultraviolet light-emitting unit, an evaporation container for accommodating neutralizer, and a catalyst device. The air dynamic unit is disposed at the inlet of the housing. The ultraviolet light-emitting unit and the catalyst device are disposed in the housing. The present invention uses the light-emitting unit and the catalyst device to purify the air and exhaust the purified air via the outlet of the housing.

9 Claims, 10 Drawing Sheets

AIR PURIFIER

FIELD OF THE INVENTION

The present invention relates generally to an air purifier, and particularly to an air purifier for neutralizing nuclear and biochemical poison gas by using a nuclear and biochemical neutralization chamber.

BACKGROUND OF THE INVENTION

The air purifying equipment according to the prior art generally adopts non-woven fabrics, active carbon, or active-carbon fibers to filter dirty air and purify the air.

If there is a substantial amount of poisonous chemical gas or biological toxicants in the air of the environment, because the biochemical poison gas is in the form of vapor or the diameter of the particles is extremely small, non-woven fabrics cannot filter completely. In addition, if active-carbon devices have inferior absorption ability for the biochemical poison gas, the problem of incomplete filtering occurs.

Currently, photocatalyst dissolution equipment is added into air purifiers. Nonetheless, the effect of oxidizing chemical poison gas or biological toxicants using photocatalyst equipment is limited. Some poison gas cannot have photolysis reactions efficiently without reacting neutralizer. Alternatively, given only photocatalyst and without other chemical neutralizer, the oxidation and reduction reactions are incomplete and limited.

Accordingly, there are still inconvenience and drawbacks in the structure and application of current air purifiers and hence improvements are highly required. For solving the problems described above, associated vendors endeavor to work out solutions. Nonetheless, for a long time, there is still no proper design developed; there is no suitable structure in general products for solving the problems described above. Apparently, the associated vendors are eager to solving these problems. Thereby, how to create an air purifier having novel structure for improving the limited effects of the air purifiers according to the prior art on purifying poison gas has become a major subject of development and the target of improvement in the industry.

SUMMARY

An objective of the present invention is to solve the problems of current air purifiers and provide a novel structure of air purifier. The technical problem to be solved is to remove or lower toxicity of biochemical poisonous materials by oxidation and reduction reactions of biochemical matters in the air with neutralizer. Thereby, the objective of purifying air can be achieved, meeting the requirement of practical utility.

Another objective of the present invention is to provide a novel structure of air purifier. The technical problem to be solved is to adopt water or boric acid as the neutralizer, which is used as the neutron fission inhibitor for radioactive matters. Thereby, the objective of reducing the harms caused by radioactive materials can be achieved, making the present invention more suitable for practical applications.

Still another objective of the present invention is to provide a novel structure of air purifier. The technical problem to be solved is to combine air purification and humidification for achieving the objective of providing a comfortable breathing environment, and thus making the present invention more suitable for practical applications.

The objectives and the technical problems to be solved by the present invention are implemented by the following technical solution. The air purifier according to the present invention comprises a housing, an air dynamic unit, a light-emitting unit, an evaporation container, and a catalyst device. The housing has an air inlet and at least an air outlet. The air dynamic unit is disposed behind the inlet, and guides air into the housing and used as the evaporation power for evaporating the neutralizer in the evaporation container. The light-emitting unit is disposed in the housing and emits ultraviolet light. The evaporation container is disposed in the housing and accommodates at least a neutralizer. The catalyst device is disposed in the housing and located on one side of the outlet. The ultraviolet light illuminates the catalyst device, which catalyzes the neutralizer to purify the air and exhausts the purified air outside the housing via the outlet.

The objectives and the technical problems to be solved by the present invention still can be implemented by the following technical meanses.

The air guided by the air dynamic unit in the air purifier described above evaporates or sublimates the neutralizer. The evaporated or sublimated neutralizer neutralizes the poisonous matters in the air.

The neutralizer of the air purifier described above is liquid or solid nuclear and biochemical neutralizer for neutralizing at least a nuclear and biochemical poisonous matter.

The neutralizer of the air purifier described above is water, which is used as a neutron inhibitor for radioactive matters. In addition, it is also used as an air humidifier for moderating the air temperature.

The air purifier described above further comprises an air-hole filtering material disposed before the inlet for filtering the air passing the inlet.

The air purifier described above further comprises an air filter disposed before the air dynamic unit for filtering the air passing the inlet.

The air purifier described above further comprises a connecting air pipe disposed between the air filer and the air dynamic unit. The air dynamic unit is connected to the air filer via the connecting air pipe and guides air into the housing. The objectives and the technical problems to be solved by the present invention still can be implemented by the following technical solution. The air purifier according to the present invention comprises a housing, an air-hole filter, and an axial fan. The housing has an inlet and at least an outlet. The air-hole filter covers before the inlet. The axial fan is disposed behind the inlet, and guides air to pass through the air-hole filter. Besides, the suction of the axial fan fixes the air-hole filter. Clean air is exhausted via the outlet.

The objectives and the technical problems to be solved by the present invention still can be implemented by the following technical solution. The air purifier according to the present invention is applied to a non-airtight chamber having a vent. The air purifier comprises a connecting pipe, a housing, an air-hole filter, and a blower. The connecting pipe is disposed behind the vent of the non-airtight chamber and connected to the inlet of the air purifier. The housing has an inlet and at least an outlet. The inlet is connected to the vent via the connecting pipe; the outlet is disposed in the non-airtight chamber. The air-hole filter is disposed before the inlet. The blower is disposed behind the inlet and the suction thereof fixes the air-hole filter. The blower guides the uncleaned air into the non-airtight chamber. The clean air enables the pressure inside the non-airtight chamber greater than the pressure of the environment outside the non-airtight chamber.

Compared with the prior art, the present invention has obvious advantages and benefits. According to the technical solutions described above, for achieving the objectives, the present invention provides an air purifier, which comprises a housing, an air dynamic unit, a light-emitting unit, and a catalyst device. The housing has an air inlet and at least an air outlet. The air dynamic unit is disposed behind the inlet, and guides air into the housing. The light-emitting unit and the catalyst device are disposed in the housing. The catalyst device is located on one side of the light-emitting unit. The catalyst device uses the ultraviolet light having high quantum energy provided by the light-emitting unit to start oxidation and reduction reactions with the poisonous matters in the air of the housing for neutralizing the nuclear and biochemical poisonous matters contained in the air. Then the purified air is exhausted from the housing via the outlet.

According to the technical solutions described above, the air purifier according to the present invention has at least the following advantages and benefits. The catalyst device and the light-emitting unit are disposed in the housing of the air purifier according to the present invention. The catalyst device and the light-emitting unit are disposed on one side of the air dynamic unit. In addition, one or more evaporation container for containing nuclear and biochemical neutralizer or water is added and used as the nuclear and biochemical neutralization chamber for nuclear and biochemical poison gas. By using the oxidation and reduction reactions between the neutralizer and the biochemical matters in the air, the toxicity of the biochemical poisonous matters in the air is lost or lowered and thus achieving the purpose of purifying air. Moreover, water and boric acid can be used as the neutralizer and act as the neutron fission inhibitor for radioactive matters in the air and hence achieving the purpose of reducing the damages of the radioactive matters in the air. In addition, the air purifier provided by the present invention further has the function of humidification. Thereby, it can further provide a more comfortable breathing environment.

To sum up, the present invention relates to an air purifier, which comprises a housing, an air dynamic unit, an ultraviolet light-emitting unit, an evaporation container for accommodating neutralizer, and a catalyst device. The air dynamic unit is disposed in the inlet of the housing; the ultraviolet light-emitting unit and the catalyst device are disposed in the housing. By using the light-emitting unit and the catalyst device according to the present invention, the air is purified and is exhausted outside the housing via the outlet.

DETAILED DESCRIPTION

In order to make the structure and characteristics as well as the effectiveness of the present invention to be further understood and recognized, the detailed description of the present invention is provided as follows along with embodiments and accompanying figures.

According to the present invention, the air dynamic unit in the air purifier installed originally (PRC utility patent application number 200820065704.7 "Air filtering device having horizontal filter by Fu-Kuo Huang, who is also the inventor of the present invention) or additionally is used as the evaporator for neutralizer. The original photocatalyst or the other catalyst device is used as the catalyst for the reaction between the vapor of the neutralizer and poisonous matters. In other words, according to the present invention, the catalyst device and the light-emitting unit are disposed in the housing and located on one side of the air dynamic unit. In addition, one or more evaporation container is placed for containing nuclear and biochemical neutralizer or water and being used as the nuclear and biochemical neutralization chamber for nuclear and biochemical poison gas. Thus, the air can be purified more efficiently.

Figure 1A:
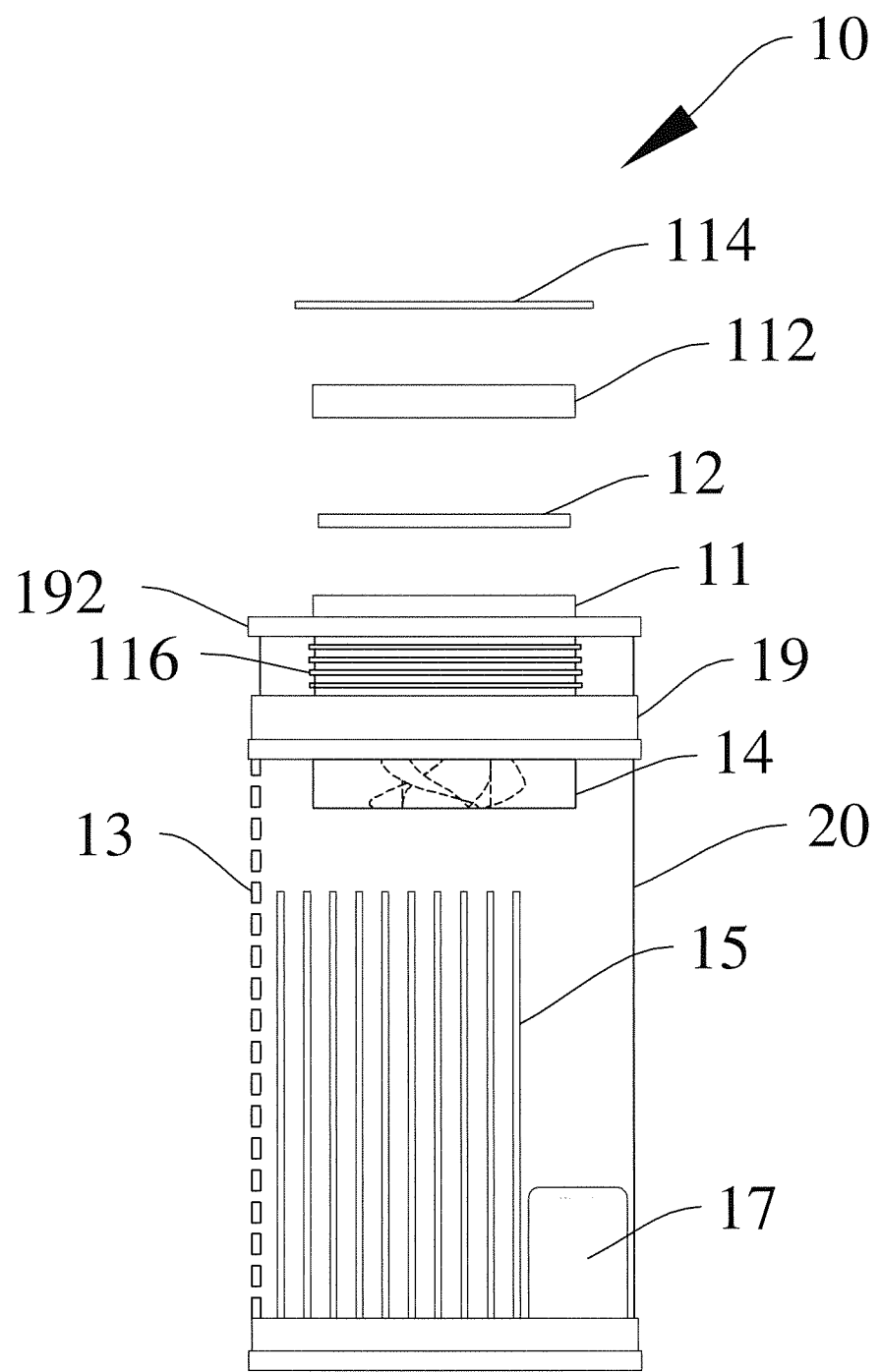
FIG. 1A shows a side view according to a preferred embodiment of the present invention.
Figure 1B:
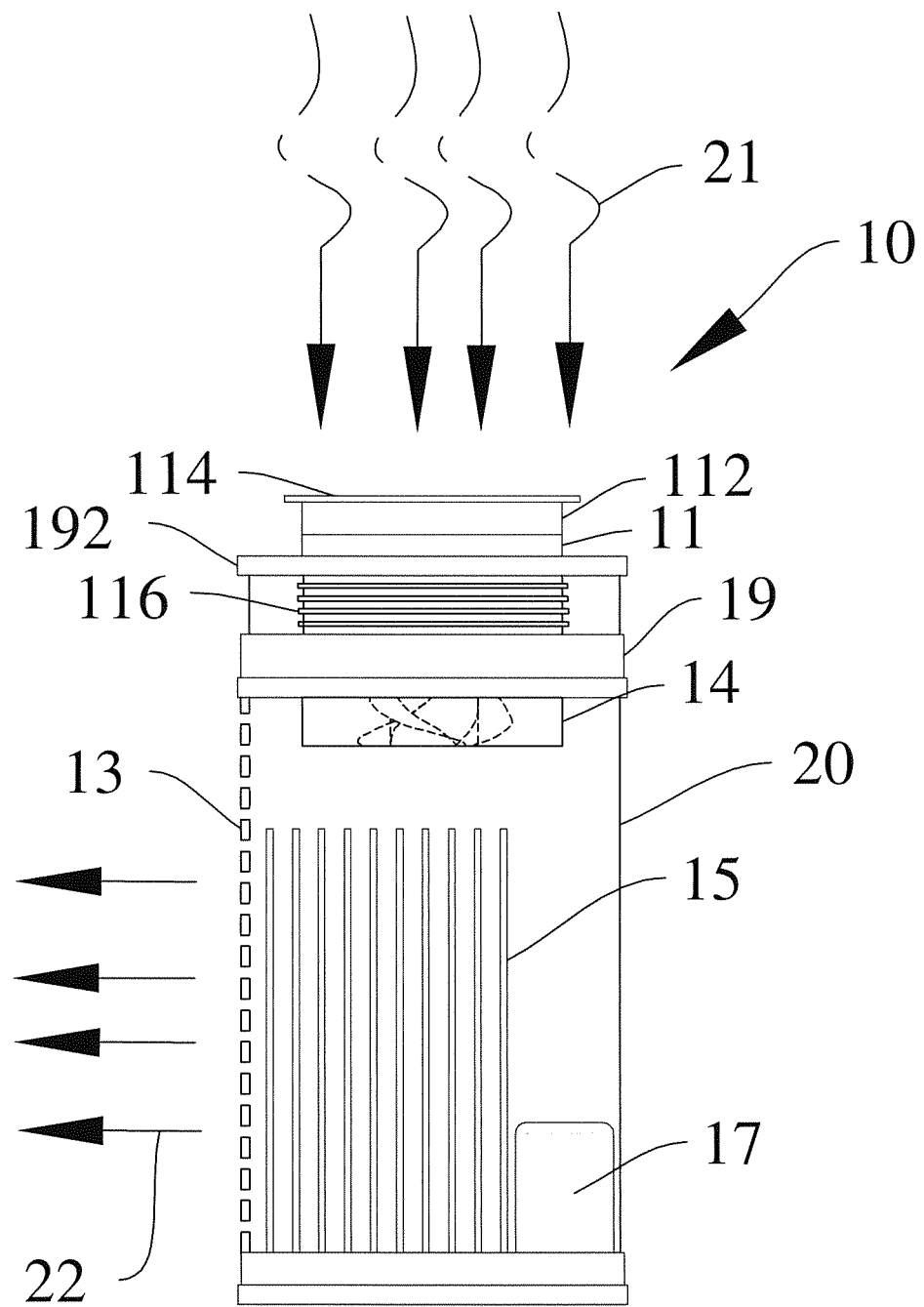
FIG. 1B shows a schematic diagram of the assembly according to a preferred embodiment of the present invention.
Figure 1C:
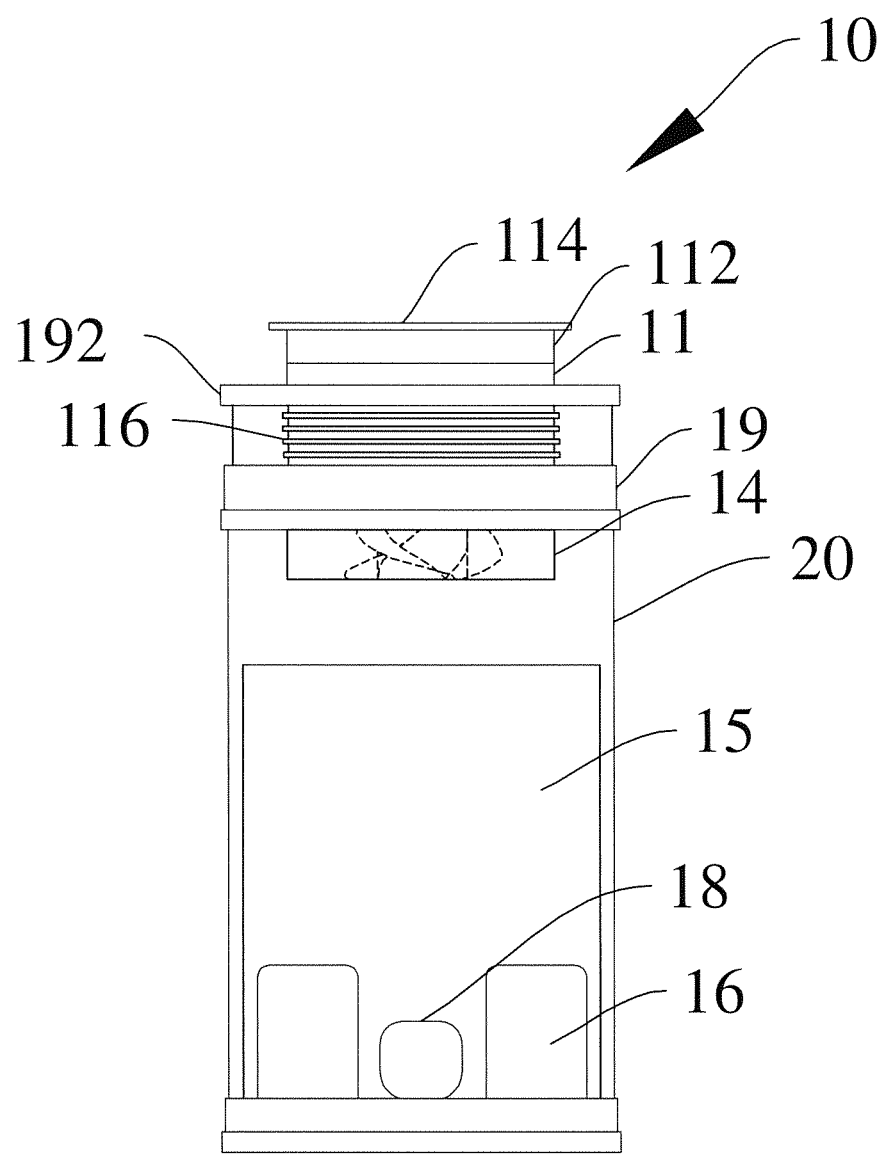
FIG. 1C shows a rear view according to a preferred embodiment of the present invention.

Please refer to FIGS. 1A to 1C. FIG. 1A shows a side view according to a preferred embodiment of the present invention; FIG. 1B shows a schematic diagram of the assembly according to a preferred embodiment of the present invention; and FIG. 1C shows a rear view according to a preferred embodiment of the present invention. As shown in the figures, the air purifier 10 according to the present invention comprises a housing 19, which includes an inlet 11, an air dynamic unit 14, and an outlet 13. An air-hole cap 112 and an air-hole filter 114 are disposed before the inlet 11. The air purifier 10 according to the present invention further comprises a catalyst device 15, a light-emitting unit 18, and an evaporation container 17.

An air filter 12 and the air dynamic unit 14 are disposed behind the inlet 11. The air filter 12 according to the present embodiment is disposed before and connected with the air dynamic unit 14. The air dynamic unit 14 according to the present embodiment is a blower, an axial fan, or a blowing machine. The catalyst device 15, the light-emitting unit 18, and the evaporation container 17 are located under the air dynamic unit 14 and disposed in the housing 19 to form a nuclear and biochemical neutralization chamber 20. The catalyst device 15 and the evaporation container 17 are both located on one side of the light-emitting unit 18; the catalyst device 15 is further located between the outlet 13 and the light-emitting unit 18. The evaporation container 17 is used for containing liquid or solid nuclear and biochemical neutralizer or water, where the water is mostly used neutron inhibitor and absorber in nuclear reactors. The light-emitting unit 18 according to the present embodiment is an ultraviolet lamps or an ultraviolet light-emitting diode, which emits ultraviolet light to fill the entire nuclear and biochemical neutralization chamber 20.

Figure 2A:
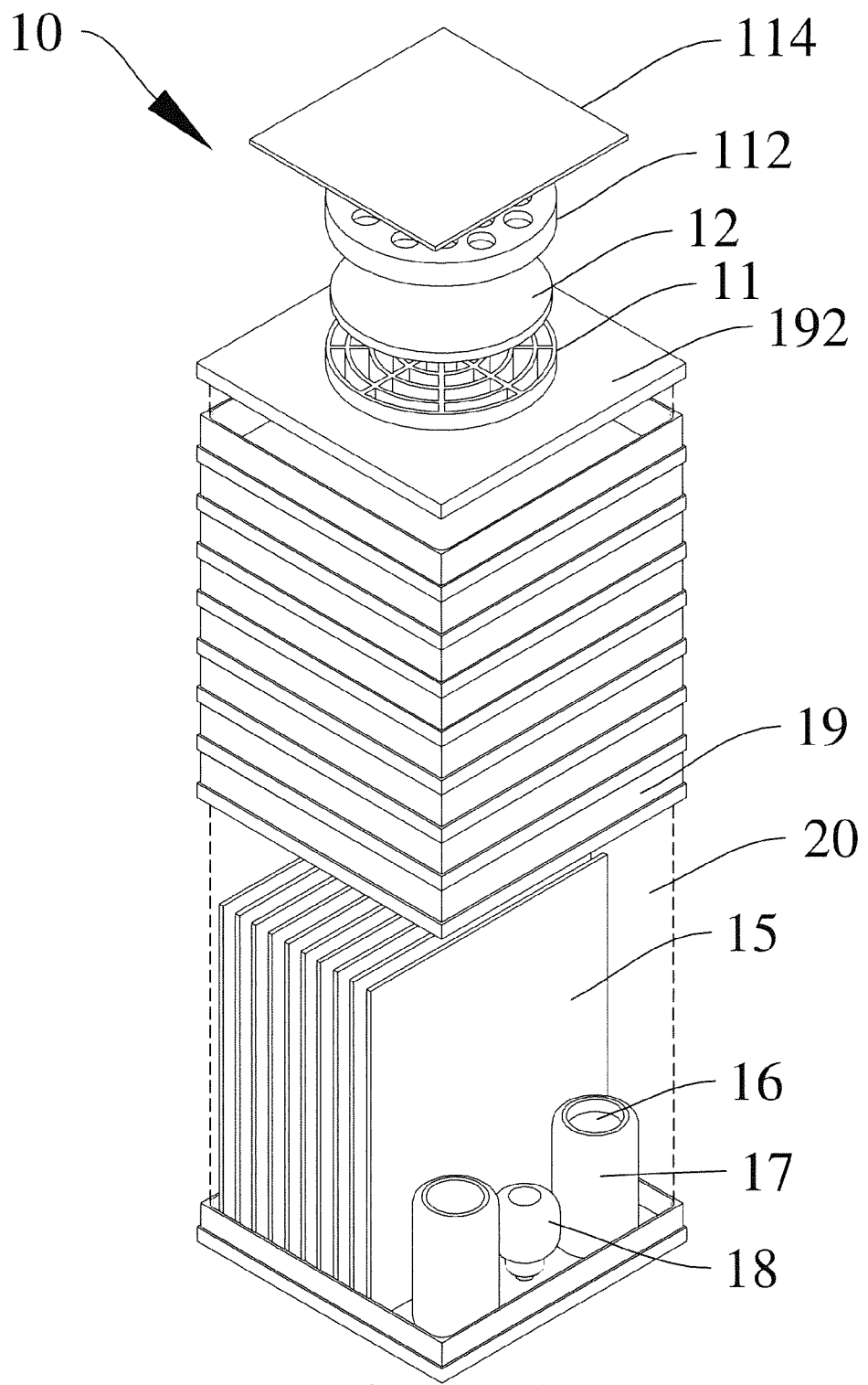
FIG. 2A shows a three-dimensional view according to a preferred embodiment of the present invention.
Figure 2B:
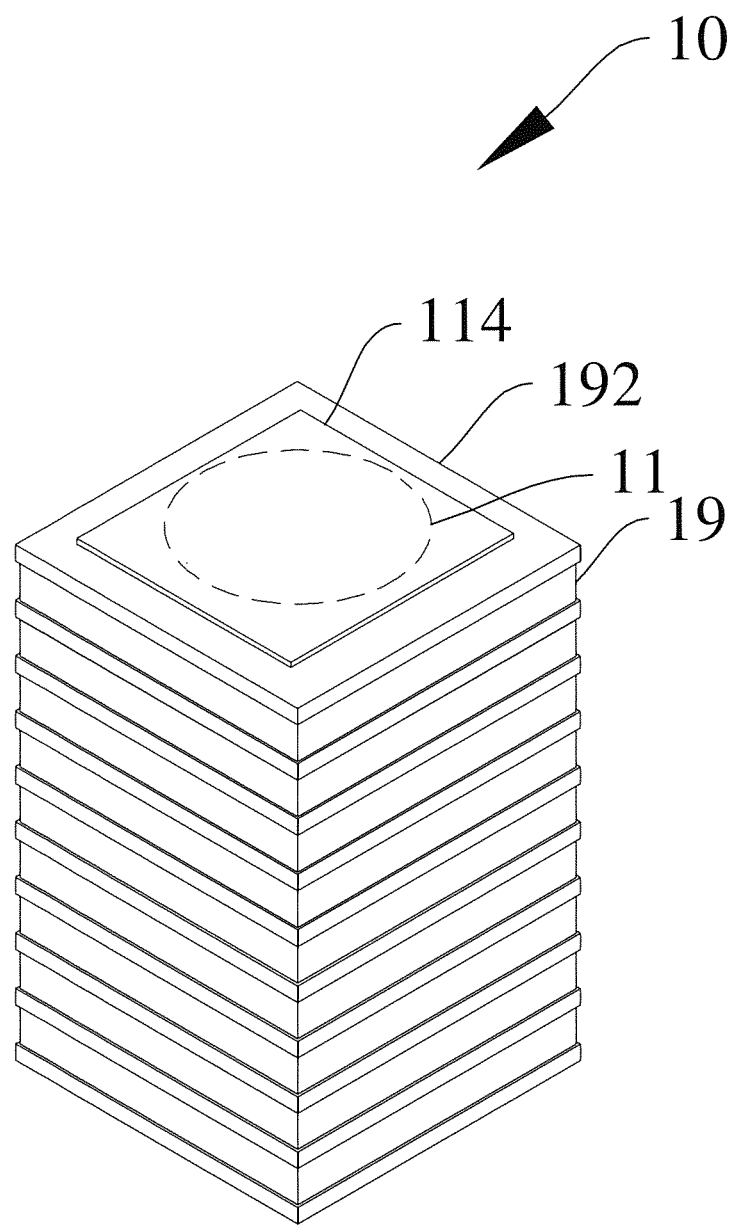
FIG. 2B shows a three-dimensional view in operating status according to a preferred embodiment of the present invention.

Please refer to FIGS. 1B, 2A and 2B. FIG. 2A shows a three-dimensional view according to a preferred embodiment of the present invention; and FIG. 2B shows a three-dimensional view in operating status according to a preferred embodiment of the present invention. The air dynamic unit 14 guides external unpurified air 21 into the housing 19. The unpurified air 21 passes the air-hole filter 114, the air-hole cap 112, the air filter 12, and a current channel 116. The it is led to the nuclear and biochemical neutralization chamber 20 inside the housing 19. Furthermore, the current power of the blower 14 is used for evaporating or sublimating the neutralizer 16 contained in the evaporation container 17 and mixing completely with the air guided into the nuclear and biochemical neutralization chamber 20. The neutralizer 16 is used for purifying the poisonous matters of the air in the nuclear and biochemical neutralization chamber 20. The catalyst device 15 can catalyze the neutralizer 16 to react with the poisonous matters in the air. Finally, the purified air is exhausted from the outlet 13.

Traditionally, the catalyst device 15 is the photocatalyst filter. Because the catalyst device 15 according to the present invention is mainly provided for the nuclear and biochemical poison gas in the nuclear and biochemical neutralization chamber 20, a part of or the whole catalyst device 15, including the photocatalyst filter, can be replaced by other catalyst filter having suitable materials, such as manganese dioxide, nickel, cobalt, platinum, and palladium.

Figure 3A:
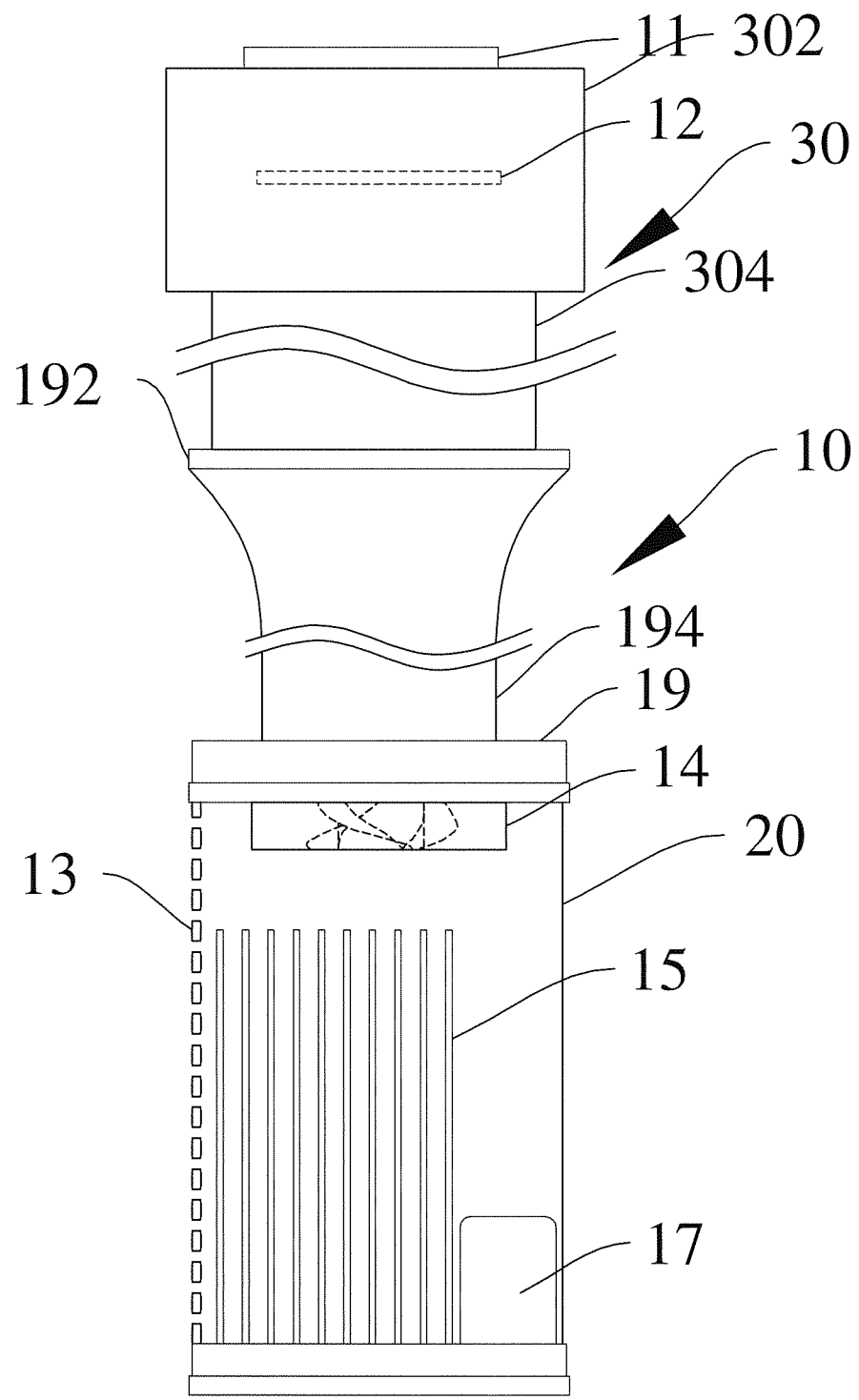
FIG. 3A shows a side view in operating status according to another preferred embodiment of the present invention.
Figure 3B:
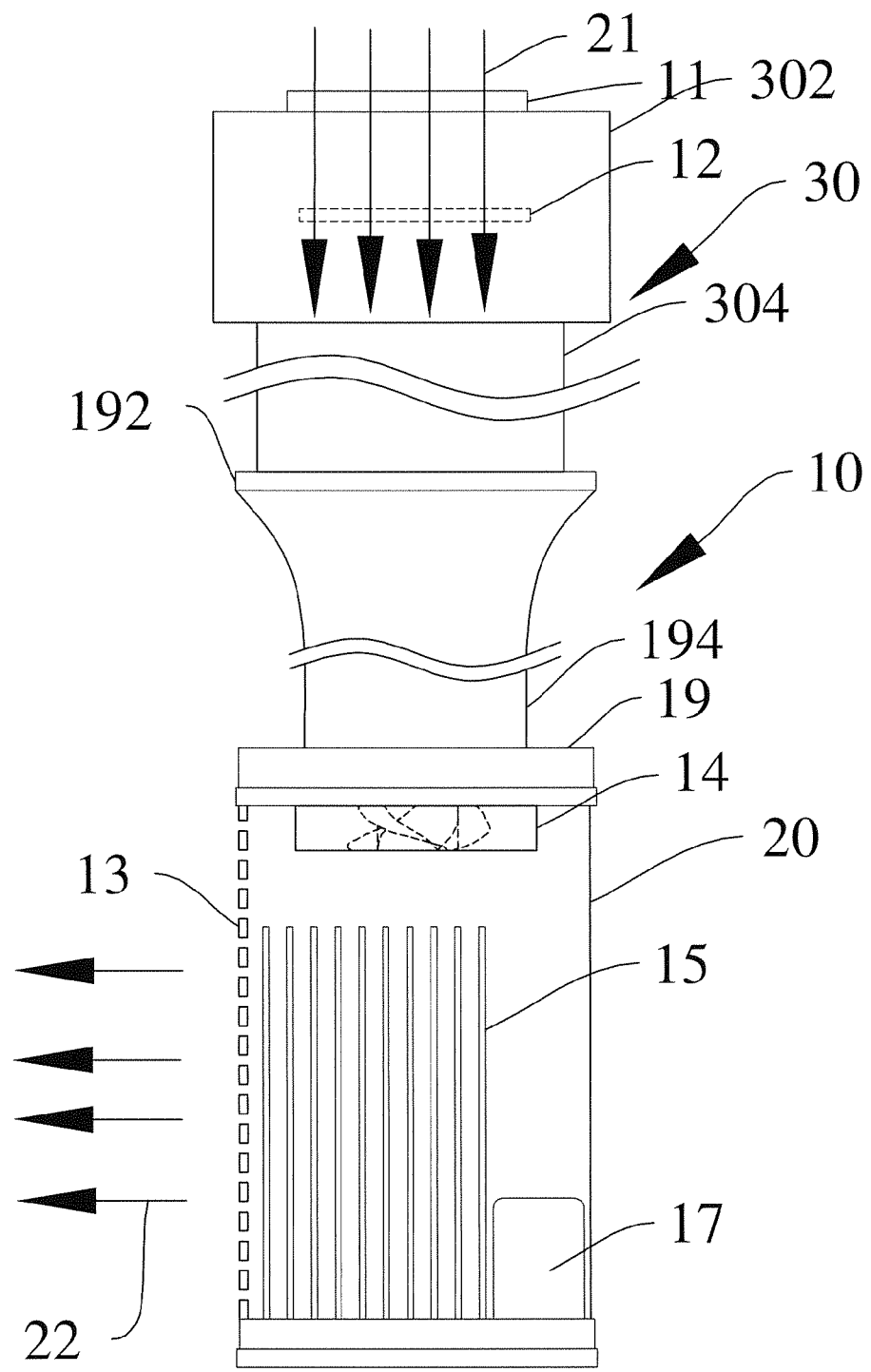
FIG. 3B shows a schematic diagram according to another preferred embodiment of the present invention.
Figure 3C:
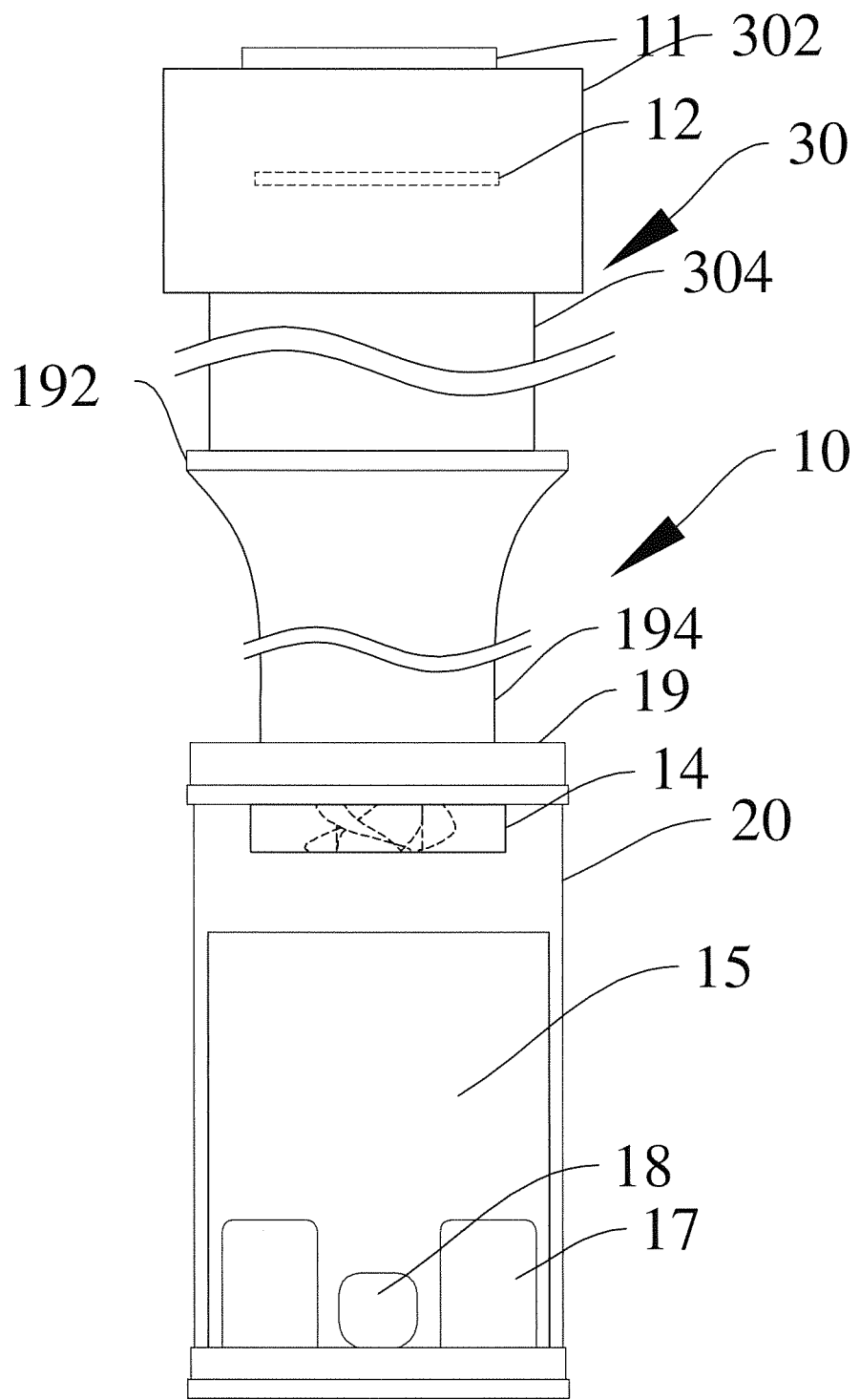
FIG. 3C shows a rear view according to another preferred embodiment of the present invention.

Please refer to FIGS. 3A to 3C. FIG. 3A shows a side view in operating status according to another preferred embodiment of the present invention; FIG. 3B shows a schematic diagram according to another preferred embodiment of the present invention; and FIG. 3C shows a rear view according to another preferred embodiment of the present invention. The difference between the FIGS. 1A to 1C and the FIGS. 3A to 3C is that the air purifier 10 in FIGS. 1A to 1C has the current channel 116 disposed between the inlet 11 and the air dynamic unit 14, while the air purifier 10 has a connecting pipe 194 disposed between the outlet 304 of the air purifier 30 and the housing 19. As shown in FIGS. 3A to 3C, the inlet 11 and the air filter 122 of the air purifier 10 according to the present invention are not disposed inside the housing 19. Instead, they are disposed in the main body 302 of another air purifier 30 and connected with the outlet 304 of the air purifier using the connecting pipe 194 for guiding the filtered air by the air purifier 30 to the air dynamic unit 14. Namely, the air purifier 10 according to the present embodiment can further work with other air purifiers for further purifying the poison gas not completely purified by other air purifiers. Then the purified air is exhausted. Thereby, by coordinating with traditional air purifiers, the present invention can enhance the purifying effect of the traditional air filtering equipment on nuclearly and biochemically contaminated air.

Figure 4:
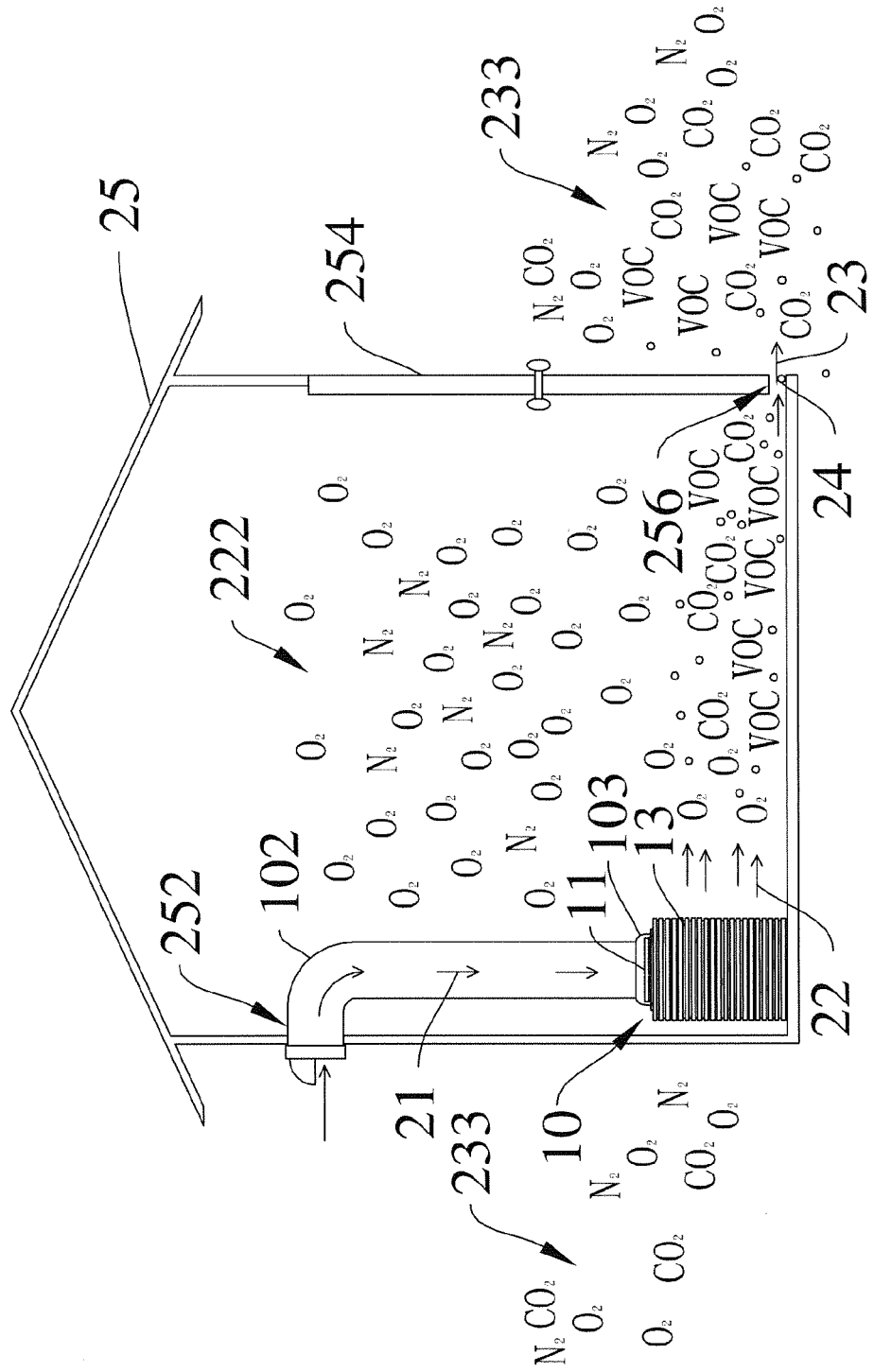
FIG. 4 shows a schematic diagram of the air purifier purifying the air according to the present invention.

Please refer to FIG. 4, which shows a schematic diagram of the air purifier purifying the air according to the present invention. As shown in the figure, the air purifier 10 according to the present invention is disposed in a non-airtight chamber 25. The non-airtight chamber 25 is a house according to the present embodiment, and includes a vent 252, a door 254, and a door crack 256. The air purifier 10 draws in the environment air 233 outside the chamber by a connecting pipe 102 passing through the vent 252, making the unpurified air flowing in the connecting pipe 102 and in the direction to the inlet 11. Then a connecting-pipe connection hood 103 is used for connecting to the air purifier 10 and guiding the unpurified air to the inlet 11 of the air purifier 10. Next, the unpurified air 21 according to the embodiment described above passes through the air-hole filter 114, the air-hole cap 112, the air filter 12, and the current channel 116, and then to the nuclear and biochemical neutralization chamber 20 inside the housing 19. Afterwards, the air is purified via the neutralizer 16 or water in the evaporation container 17 as well as the catalyst device 15. The clean air is exhausted via the outlet 13 and into the non-airtight chamber 25 for diluting the exhaust gas 23 and dust 24 contained in the positive-pressure space air 222. Thus, pressure will increase in the non-airtight chamber 25 and forming the positive-pressure space air 222. The pressure of the positive-pressure space air 222 will leak via the door crack 256. Thereby, the relation of the magnitutude of pressure is as follows:

Clean air 22>Pressure of the non-airtight chamber 25 (Positive-pressure space air 222)>Poisonous exhaust gas 23>Environment air 233 outside the chamber>Unpurified air 21

The pressure in the non-airtight chamber 25 is greater than the pressure of the environment air 233 outside. Thereby, the positive-pressure space air 222 will exhaust the poisonous exhaust gas 23, such as volatile organic compounds (VOC) and carbon dioxide ($CO_2$), and dust 24 outside the chamber via the door crack 256 and the completes pressure release. The balancing between the pressure in the non-airtight chamber 25 and the pressure outside is thus performed continuously.

According to the present embodiment, the clean air 22 is injected continuously into the non-airtight chamber 25 for diluting the exhaust gas 23 and the dust 24 contained in the positive-pressure space air 22 and thus pushing the poisonous exhaust gas 23 and the dust 24 out of the chamber gradually. In addition, thanks to the pressure, pollution of the environment air 233 outside the chamber on the positive-pressure space air 22 can be avoided by stopping the environment air 233 from entering the non-airtight chamber 25 via the door crack 256. In addition to the house according to the previous embodiment, the non-airtight chamber 25 can also be a container space, a closet, a cabin, or an internal space of a car.

Figure 5:
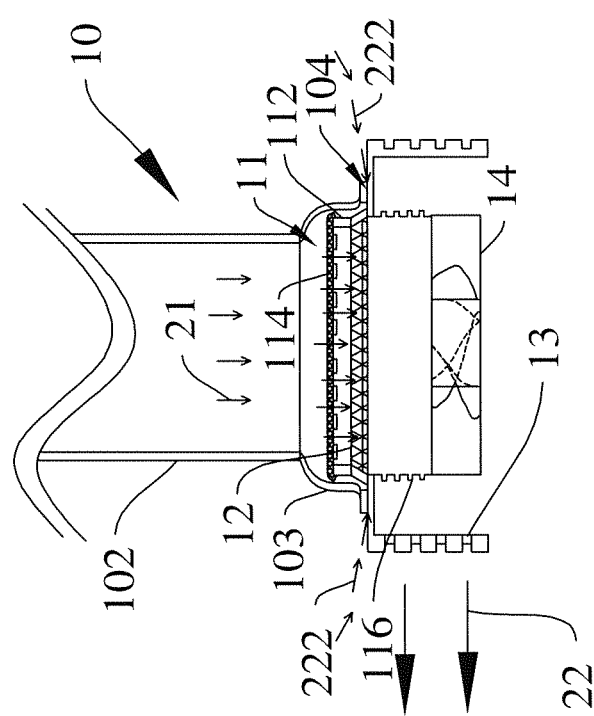
FIG. 5 shows a cross-sectional view of the inlet of the air purifier according to the present invention.

Please refer to FIG. 5, which shows a cross-sectional view of the inlet of the air purifier according to the present invention. As shown in the figure, the air purifier 10 according to the present invention is disposed on the inlet 11 by means of a connecting-pipe connection hood 103 and connected with the connecting pipe 102. The connecting-pipe connection hood 103 covers the air-hole filter 114 and the air-hole cap 112. In addition, the air filter 12 is disposed between the air-hole cap 112 and the air dynamic unit 14. The air dynamic unit 14 according to the present embodiment is a blower; the air filter according to the present embodiment includes active carbon fibers. The air dynamic unit 13 draws in the unpurified air 21 in the connecting pipe 102 and enables it to flow in the direction to the inlet 11 and pass through the air-hole filter 114 and the air filter 12. Because of the suction by the air dynamic unit 14, the pressure of the unpurified air will be reduced immediately, making the pressure of the positive-pressure space air 222 much greater than the reduced pressure of the unpurified air 21. Accordingly, taking the positive-pressure space air 222 as the environment pressure, the unpurified air 21 in the connecting pipe 102 is not able to leak from the connecting gap 104 because the environment pressure, namely, the positive-pressure space air 222, is much greater than the reduced pressure of the unpurified air 21. According to the physical principle that higher pressure flows to the lower pressure, it is guaranteed that the unpurified air 21 will not pollute the air quality of the positive-pressure space air 222 in the non-airtight chamber 25 due to leakage.

Moreover, the air purifier 10 according to the present invention can further use the evaporation container 17 to contain water. The water vapor and the clean air are mixed completely and before exhaust. Thereby, the air temperature is moderated and the air humidity is increased; the air purifier 10 can thus used as a cold humidifier.

To sum up, the present invention provides an air purifier, which comprises a nuclear and biochemical neutralization chamber for purifying nuclear and biochemical poison gas effectively. In addition, the present invention can also be used as a cold humidifier for moderating the air temperature as well as increasing the air humidity. Thereby, the present invention can simplify substantially the structure and costs of the filtering equipment for nuclear and biochemical poison gas.

The original and extended functions of the ultraviolet light and the catalyst device in the air purifier are described as follow:

1. The ultraviolet light provides high-quantum-energy operating energy for oxidation and reduction reactions with the functions of:

providing the energy source for the oxidation and reduction reactions for the catalyst device; and providing the energy source for the oxidation and reduction reactions between the neutralizer and the nuclear and biochemical matters.

2. The catalyst device is a device for catalyzing the neutralization reaction. Its functions are described as follows:

The photocatalyst device acquires the energy supplied by the ultraviolet light and has the function of dissolving organic matters directly.

The catalyst device acquires the energy supplied by the ultraviolet light and has the function of catalyzing the oxidation and reduction reaction between the neutralizer and the nuclear and biochemical poison gas.

3. Water can be added into the evaporation container. The functions are described as follows:

The major purpose of evaporating water is to provide water vapor and used as the neutralizer of the oxidation and reduction reaction for the biochemical poison gas and as the neutron moderator for radioactive matters. Neutron moderator is also known as neutron inhibitor; water vapor is the mostly used neutron moderator and absorber in nuclear reactors.

The secondary purpose of evaporating water is to provide water vapor to mix with air for moisturizing the air and moderating the air temperature.

Accordingly, the present invention conforms to the legal requirements owing to its novelty, nonobviousness, and utility. However, the foregoing description is only embodiments of the present invention, not used to limit the scope and range of the present invention. Those equivalent changes or modifications made according to the shape, structure, feature, or spirit described in the claims of the present invention are included in the appended claims of the present invention.

The invention claimed is:

1. An air purifier, comprising:
   a housing, having an inlet and at least an outlet;
   an evaporation container, disposed in said housing, and accommodating at least a neutralizer;
   an air dynamic unit, disposed behind said inlet, guiding air into said housing, and used as the evaporating power for said neutralizer in said evaporation container;
   a light-emitting unit, disposed in said housing, and emitting ultraviolet light; and
   a catalyst device, disposed in said housing and located on one side of said outlet, said ultraviolet light illuminating said catalyst device, and said catalyst device catalyzing said neutralizer to purify air and exhausting the purified air out of said housing via said outlet.

2. The air purifier of claim 1, wherein the air guided by said air dynamic unit evaporates or sublimates said neutralizer, and said evaporated or sublimated neutralizer neutralizes the poisonous matters in said air.

3. The air purifier of claim 2, wherein said neutralizer is liquid or solid nuclear and biochemical neutralizer for neutralizing at least a nuclear and biochemical poisonous matter.

4. The air purifier of claim 2, wherein said neutralizer is water used as the neutron moderator for a radioactive matter and further as an air humidifier for moderating the air temperature.

5. The air purifier of claim 1, and further comprising an air-hole filter disposed before said inlet for filtering the air passing through said inlet.

6. The air purifier of claim 1, and further comprising an air filter disposed before said inlet for filtering the air passing through said inlet.

7. The air purifier of claim 6, and further comprising a connecting pipe disposed between said air filter and said air dynamic unit, and said air dynamic unit connecting to said air filter via said connecting pipe and guiding air into said housing.

8. An air purifier, comprising:
   a housing, having an inlet and at least an outlet;
   an air-hole filter, disposed before and covering said inlet; and
   an axial fan, disposed behind said inlet, guiding air to pass through said air-hole filter, fixing said air-hole filter using the suction of said axial fan, and exhausting clean air via said outlet.

9. An air purifier, applied to a non-airtight chamber having a vent, and comprising:
   a connecting pipe, disposed behind said vent of said non-airtight chamber, and connecting with an inlet of said air purifier;
   a housing, having said inlet and at least an outlet, said inlet connected to said vent via said connecting pipe, and said outlet disposed in said non-airtight chamber;
   an air-hole filter, disposed before said inlet; and
   a blower, disposed behind said inlet, the suction of said blower fixing said air-hole filter, guiding unpurified air to pass through said air-hole filter and transporting into said housing, exhausting clean air to said non-airtight chamber via said outlet, and said clean air enabling the pressure inside said non-airtight chamber greater than the pressure of the environment outside said non-airtight chamber.

* * * * *